(12) United States Patent
Göhring

(10) Patent No.: US 6,274,734 B1
(45) Date of Patent: Aug. 14, 2001

(54) PROCESS FOR MAKING PYRIMIDINE DERIVATIVES

(75) Inventor: Wolfgang Göhring, Steinen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/526,252

(22) Filed: Mar. 16, 2000

Related U.S. Application Data

(62) Division of application No. 09/161,086, filed on Sep. 25, 1998, now Pat. No. 6,121,447, which is a division of application No. 08/951,700, filed on Oct. 16, 1997, now Pat. No. 5,883,254.

Foreign Application Priority Data

Nov. 8, 1996 (CH) .................................................. 2757/96

(51) Int. Cl.[7] .................................................. C07D 403/04
(52) U.S. Cl. ........................... 544/330; 544/320; 544/298
(58) Field of Search .................................... 544/298, 320, 544/330, 332

(56) References Cited

U.S. PATENT DOCUMENTS 3,178,254 * 4/1965 Hoelzle et al. ........................ 8/54.2

* cited by examiner

Primary Examiner—John M. Ford

(74) Attorney, Agent, or Firm—George W. Johnston; William H. Epstein; John P. Parise

(57) ABSTRACT

The present invention provides a process for the manufacture of pyrimidines of formula I:

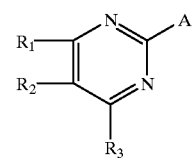

wherein
$R^1$, $R^2$, $R^3$ each independently represent hydrogen, $C_{1-7}$-alkyl, or $C_{1-7}$-alkoxy, A signifies
—CN,
a carbanionic $R^4$-alkynyl residue, in which $R^4$ is hydrogen or $C_{1-7}$-alkyl, or
a carbanionic residue of the malonic acid derivative of formula III

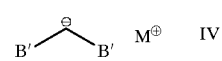

in which B and B' independently represent —CN, —COOR$^5$, or —C(O)R$^5$,
wherein $R^5$ is alkyl or aryl.

6 Claims, No Drawings

PROCESS FOR MAKING PYRIMIDINE DERIVATIVES

CROSS REFERENCE TO RELATED APPLICATIONS

This is a divisional of application Ser. No. 09/161,086 filed on Sep. 25, 1998, now U.S. Pat. No. 6,121,447, which is a divisional of application Ser. No. 08/951,700 filed on Oct. 16, 1997, which is now U.S. Pat. No. 5,883,254.

BACKGROUND OF THE INVENTION

The present invention provides a new process for the preparation of pyrimidine derivatives.

SUMMARY OF THE INVENTION

The subject process for manufacturing a compound of the formula:

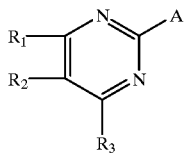

I $R^1$, $R^2$, $R^3$ each independently is hydrogen, $C_{1-7}$-alkyl, or $C_{1-7}$-alkoxy, and A is —CN, which comprises reacting a compound of the formula:

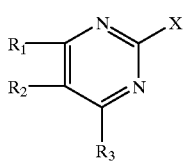

II wherein $R^1$, $R^2$ and $R^3$ are as above and X is chlorine, with an alkali cyanide in the presence of 1-azabicyclo[2,2,2]octane or 1,4-diazabicyclo[2,2,2]octane.

Of particular concern is a process for manufacturing 2-cyanopyrimidine, which comprises reacting 2-chloropyrimidine with an alkali cyanide in the presence of 1-azabicyclo-[2,2,2]octane or 1,4-diazabicyclo[2,2,2]octane.

Another particularly useful process is for manufacturing 4-tertbutyl-N-6-(2-hydroxy-ethoxy)-5-(2-methoxy-phenoxy)-2-(pyrimidin-2-yl)-pyrimidin-4-yl-benzenesulphonamide, This process comprises manufacturing 2-cyanopyrimidine by reacting 2-chloropyrimidine with an alkali cyanide in the presence of 1-azabicyclo[2,2,2]octane or 1,4-diazabicyclo[2,2,2]octane. The 2-cyano pyrimidine is then converted by means of $NH_3/NH_4Cl$ in a sodium methanolate/methanol solution into pyrimidin-2-carboxamidine hydrochloride. The pyrimidine-2-caroboxamidine hydrochloride is then converted in the presence of sodium methanolate with diethyl (o-methoxy-phenoxy-malonate) into rac-5-(2-methoxy-phenoxy)-2-pyrimidin-2-yl-tetrahydro-pyrimidin-4,6-dione. This product is then reacted with N,N-diisopropyl-N-ethylamine and phosphorus pentachloride to give 4,6-dichloro-5-(2-methoxy-phenoxy)-2,2'-bipyrimidine. This in turn is reacted with p-tert.butylbenzenesulphonamide to give 4-tert.butyl-N-6-chloro-5-[2-(2-methoxy-phenoxy)-2-(pyrimidin-2-yl)-pyrimidin-4-yl]-benzenesulphonamide which is reacted with sodium ethylene glycolate to give 4-tert.butyl-N-6-(2-hydroxy-ethoxy)-5-(2-methoxy-phenoxy)-2-(pyrimidin-2-yl)-pyrimidin-4-yl-benzenesulphonamide.

Intermediates in the above process include a compound of the formula:

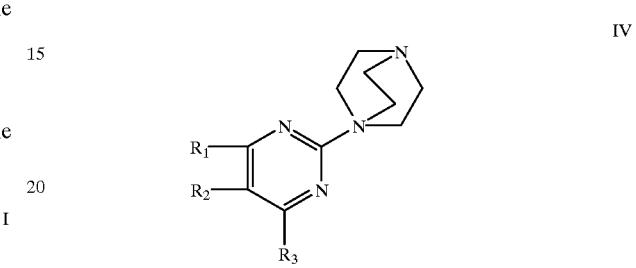

IV wherein $R^1$, $R^2$, $R^3$ each independently is hydrogen, $C_{1-7}$-alkyl, or $C_{1-7}$-alkoxy, and salts thereof; and a compound of the formula:

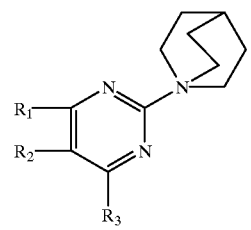

V wherein $R^1$, $R^2$, $R^3$ each independently is hydrogen, $C_{1-7}$-alkyl, or $C_{1-7}$-alkoxy, and salts thereof.

DETAILED DESCRIPTION OF THE INVENTION

The subject invention will now be described in terms of its preferred embodiments. These embodiments are set forth to aid in understanding the invention, but are not to be construed as limiting.

In detail, the subject invention relates to a novel process for the manufacture of pyrimidines of formula I:

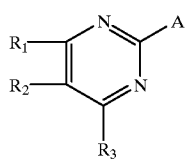

I wherein $R^1$, $R^2$, $R^3$ each independently represent hydrogen, $C_{1-7}$-alkyl, or $C_{1-7}$-alkoxy, A signifies

—CN, a carbanionic $R^4$-alkynyl residue, in which $R^4$ is hydrogen or $C_{1-7}$-alkyl, or a carbanionic residue of the malonic acid derivative of formula III

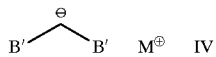
    IIIm in which B and B' independently represent —CN, —COOR$^5$, or —C(O)R$^5$, wherein R$^5$ is alkyl or aryl.

The process is useful for the preparation of pharmaceutical products, for example, those described in European Patent Application Publ. No. 726,708.

A first aspect of the present invention relates to a process which comprises reacting a pyrimidine of the formula:

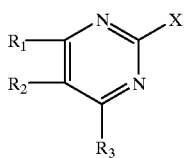
    II wherein $R^1$, $R^2$ and $R^3$ have the above significances and X is chlorine, with a compound yielding the residue A in the presence of 1-azabicyclo[2,2,2]octane (ABCO) or 1,4-diazabicyclo[2,2,2]octane (DABCO).

A second aspect of this invention relates to intermediates of formulas IV and V or salts thereof:

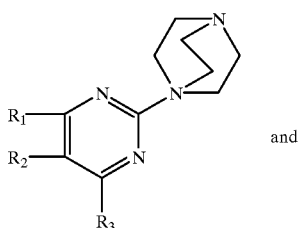
    IV and

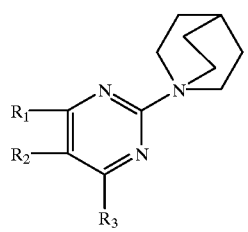
    V wherein $R^1$, $R^2$, $R^3$ each independently represent hydrogen, $C_{1-7}$-alkyl, or $C_{1-7}$-alkoxy.

In more detail, the present invention refers to a process for the manufacture of pyrimidines of the formula I:

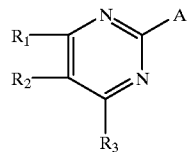
    I wherein $R^1$, $R^2$, $R^3$ each independently represent hydrogen, $C_{1-7}$-alkyl, or $C_{1-7}$-alkoxy, A signifies
—CN,
a carbanionic $R^4$-alkynyl residue, in which $R^4$ is hydrogen or $C_{1-7}$-alkyl, or
a carbanionic residue of the malonic acid derivative of formula III:

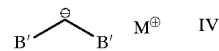
    III in which B and B' independently represent —CN, —COOR$^5$, or —C(O)R$^5$, wherein R$^5$ is alkyl or aryl.

which process comprises reacting a pyrimidine of the formula:

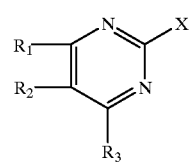
    II wherein $R^1$, $R^2$ and $R^3$ have the above significances and X is chlorine, with a compound yielding the residue A in the presence of 1-azabicyclo[2,2,2]octane or 1,4-diazabicyclo[2,2,2]octane.

The starting compounds, pyrimidine derivatives of formula II, can be prepared from the corresponding 2-pyrimidone (2-hydroxypyrimidine) derivatives ("The chemistry of heterocyclic compounds", Ed. E. C. Taylor, Vol. 52, "The Pyrimidines", John Wiley & Sons, N.Y., 1994). For example, the corresponding 2-pyrimidone (2-hydroxypyrimidine) can be reacted with PCl$_5$, POCl$_3$ or a combination of PCl$_5$ and POCl$_3$. The resulting 2-chloropyrimidine derivative can be used for the process of the present invention.

In the present invention the term "alkyl" signifies a straight-chain or branched alkyl group containing 1 to 7 carbon atoms, preferably 1 to 3 carbon atoms, such as methyl, ethyl, n-propyl, iso-propyl, n-butyl, iso-butyl, tertbutyl, n-pentyl, iso-pentyl, neopentyl, n-hexyl, isohexyl and isohexyl. The term "alkoxy" means the group —O—R wherein R is alkyl as defined above.

The term "aryl" means a monocyclic or bicyclic aromatic ring, preferably phenyl or naphthyl, and most preferably phenyl, which optionally can be substituted in the ortho-, meta- and/or para-position. Substituents which come into consideration are alkyl, alkoxy, hydroxy, nitro, trifluoromethyl as well as halo such as fluorine, chlorine, bromine and iodine or also trialkylsilyl. Preferred aryl residues are phenyl, p-tolyl, m-tolyl, m,m'-dialkylphenyl, p-chlorophenyl and p-methoxyphenyl.

The term "carbanionic residue" refers to residues resulting from base treatment of alkynyls or malonic acid derivatives, for example, carbanionic $R^4$-alkynyl residues wherein $R^4$ is alkyl or hydrogen. Examples of $R^4$-alkynyl residues are acetylene, propyne and 1-butyne, which can be converted by alcoholates and other bases into the carbanionic residue.

Further examples of carbanionic residues are carbanionic residues of malonic acid derivatives of formula III

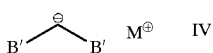

in which B and B' independently represent —CN, —COOR$^5$, or —C(O)R$^5$, wherein $R^5$ is alkyl or aryl. Examples for these carbanionic residues are acetoacetic ester and its higher homologues, which have been converted by for example by a metal hydride into the reactive carbanionic component A.

One preferred process includes pyrimidines of general formula II in which $R^1$, $R^2$ and $R^3$ are each independently hydrogen, $C_{1-3}$-alkyl, or $C_{1-3}$-alkoxy as starting material. In the most preferred embodiment $R^1$, $R^2$ and $R^3$ are all hydrogen (2-chloropyrimidine).

Another preferred category refers to the compounds yielding the residue A. In a preferred embodiment the above pyrimidine compounds of formula II are reacted with a compound yielding the residue A wherein A signifies —CN or a carbanionic residue of a malonic acid derivative of formula III

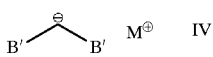

in which B and B' independently represent —CN, —COOR$^5$, or —C(O)R$^5$, wherein $R^5$ is alkyl or aryl. In a more preferred embodiment $R^5$ is alkyl. In general, the carbanionic residues of formula III can be prepared e.g. from malonic acid esters and malonic acid derivatives using a metal hydride such as sodium hydride, lithium aluminium hydride and the like.

In the most preferred embodiment the above pyrimidines of general formula II are reacted with a compound yielding the residue A wherein A is —CN. The reagents yielding this cyano group can be, for example, alkali cyanides such as sodium cyanide.

As solvents there can be used organic aprotic, non-polar or polar solvents from the group of halogenated hydrocarbons such as methylene chloride or chloroform, DMF, DMSO, N-methylpyrrolidine, acetonitrile, sulpholane, esters from the group of methyl acetate, ethyl acetate and propyl acetate or ethers such as tetrahydrofuran either alone in admixture with one another or with water. DMF, DMSO, N-methylpyrrolidine, acetonitrile, sulpholane, methylene chloride, chloroform as well as trifluoromethylbenzene are preferred.

Preferably, an alkali cyanide, especially sodium cyanide, is reacted with compounds of formula II, preferably 2-chloropyrimidine. When an alkali cyanide, especially sodium cyanide, is used, the compound of formula II is preferably reacted in an equivalent ratio of 0.1 to 1.4.

The aforementioned 1-azabicyclo[2,2,2]octane or 1,4-diazabicyclo[2,2,2]octane can be used as catalysts. These compounds are commercially available (Fluka, etc.). 1,4-Diazabicyclo[2,2,2]octane (DABCO) is especially preferred. The catalyst is used in the process in accordance with the invention in amounts of 0.001 to 1.5, preferably 0.05 to 0.8, mol equivalents based on the compound of formula II. When 1,4-diazabicyclo[2,2,2]octane is used, the most preferred amount of catalyst is 0.05 to 0.2 molar equivalents based on compound II.

The course of the reaction is conveniently monitored by an in-process control in which the ratio of educt (for example chloropyrimidine) to product (for example cyanopyrimidine) is the determining criterion for stopping the reaction. The reaction is stopped when the critical limit has been reached.

The working up of the reaction product can be effected using means which are known per se, for example, extraction with solvents. For example, the reaction mixture can be firstly diluted with water and thereupon subsequently extracted several times with TBME and n-hexane.

The reaction temperature conveniently amounts to about 20° to 60° C. Using calorimetric investigations it has been established that higher yields can be achieved at temperatures below 40° C. than at higher reaction temperatures. The reaction temperature is therefore preferably 15–35° C.

The most preferred process refers to the preparation of 2-cyano-pyrimidine which process comprises reacting 2-chloropyrimidine with an alkali cyanide in the presence of 1-azabicyclo[2,2,2]octane or 1,4-diazabicyclo[2,2,2]octane, preferably diazabicyclo[2,2,2]octane.

The process of the present invention is useful for the preparation of valuable intermediates for the synthesis of pyrimidine derivatives. Compounds of formula I in which A is —CN can be converted into pharmaceutically active substances useful as inhibitors of endothelin receptors. They can be used for the treatment of disorders which are associated with endothelin activities, especially circulatory disorders such as hypertension, ischaemia, and angina pectoris.

Compounds of formula I in which A is —CN may be converted in the corresponding carboxamidine, e.g. by $NH_3$/$NH_4Cl$. This derivative may then be used in the manner described in European Patent Application Publ. No. 726,708 to produce inhibitors of endothelin receptors.

For the preparation of the inhibitors according to EP 726,708, a compound of formula I in which A is —CN is converted for example by means of $NH_3/NH_4Cl$ into the corresponding carboxamidine. This substance may then be converted with a phenoxy-malonate into a pyrimidinyl-tetrahydro-pyrimidine-dione, which is then reacted with phosphorus pentachloride followed by a reaction with a benzenesulphonamide to give the corresponding benzenesulphonamide derivative which may then be converted into a pharmaceutically active substance by reaction with a for example an alkali glycolate corresponding to the desired end product.

The process of the present invention is especially useful for the preparation of 4-tert.butyl-N-6-(2-hydroxy-ethoxy)-5-(2-methoxy-phenoxy)-2-(pyrimidine-2-yl)-pyrimidine-4-yl-benzenesulphonamide (bosentan). For the preparation of this compound 2-cyanopyrimidine is prepared as described above and converted into pyrimidin-2-carboxamidine hydrochloride by means of $NH_3/NH_4Cl$ in a sodium methanolate/methanol solution. This compound is converted in the presence of sodium methanolate with diethyl (o-methoxy-phenoxy-malonate) into rac-5-(2-methoxy-phenoxy)-2-pyrimidin-2-yl-tetrahydro-pyrimidin-4,6-dione. The obtained product is reacted with N,N-diisopropyl-N-ethylamine and phosphorus pentachloride to give 4,6-dichloro-5-(2-methoxy-phenoxy)-2,2'-bipyrimidine. This substance is then reacted with p-tert.butylbenzenesulphonamide to give 4-tert.butyl-N-6-chloro-5-[2-(2-methoxy-phenoxy)-2-(pyrimidin-2-yl)-pyrimidin-4-yl]-benzenesulphonamide and further reacted with sodium ethylene glycolate to give 4-tert.butyl-N-6-(2-hydroxy-ethoxy)-5-(2-methoxy-phenoxy)-2-(pyrimidin-2-yl)-pyrimidin-4-yl-benzenesulphonamide (bosentan).

The present invention accordingly includes the use of the process in accordance with the invention for the production of bosentan.

It has been found that in the reaction in accordance with the invention the intermediate compounds of the formulas IV and V or salts thereof, preferably chlorides:

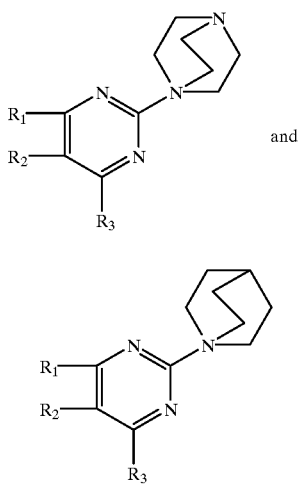

and wherein $R^1$, $R^2$, $R^3$ each independently represent hydrogen, $C_{1-7}$-alkyl, or $C_{1-7}$-alkoxy are obtained by reaction of the catalysts with compounds of formula II. Especially preferred compounds are those wherein $R^1$, $R^2$ and $R^3$ are each independently hydrogen, $C_{1-3}$-alkyl, or $C_{1-3}$-alkoxy. The most preferred compounds are 1-pyrimidin-2-yl-4-aza-1-azonium-bicyclo[2,2,2]octane chloride and 1-pyrimidin-2-yl-1-azonium-bicyclo[2,2,2]octane chloride. These compounds are also an object of the present invention and can be obtained in isolated form conveniently by reacting a compound of formula II with ABCO or DABCO in toluene at room temperature.

The following Examples illustrate the invention. In these Examples the abbreviations used have the following significance:

| | |
|---|---|
| RT | Room temperature |
| GC | Gas chromatography |
| ABCO | 1-Azabicyclo[2,2,2]-octane |
| DABCO | 1,4-Diazabicyclo[2,2,2]-octane |
| DMF | Dimethylformamide |
| DMSO | Dimethyl sulphoxide |
| TBME | tert-Butyl methyl ether |

EXAMPLE 1

26.25 g (1.05 equivalents) of sodium cyanide, 5.63 g (0.1 equivalent) of DABCO and a solvent mixture of DMSO and water were placed in a sulphonation flask at a temperature of 20 to 25° C. A solvent mixture of 150 ml of DMSO and 57.55 g of 2-chloropyrimidine was added to the pre-prepared solution using a dropping funnel at a temperature of 20 to 30° C. over a period of 15 minutes. The mixture was held at 20–22° C. for a further 2 hours while stirring. During the reaction a weak stream of nitrogen was conducted through the reactor and subsequently through a 2N NaOH solution in order to trap excess hydrogen cyanide which results.

After less than 3% of the educt used in the reaction mixture was present the reaction was interrupted and the reaction mixture was worked up.

The working up of the reaction mixture was effected by extraction with TBME and n-hexane. Yield of 2-cyanopyrimidine 96.5%.

EXAMPLE 2–7

Examples 2 to 7 were carried out analogously to Example 1 using different organic solvents. The yields will be evident from Table 1.

TABLE 1

| Example | Org. solvent/water | Isolated yield (%) |
|---|---|---|
| 2 | tert.-Butyl methyl ether | 51 |
| 3 | Toluene | 60 |
| 4 | Diethoxymethane | 71 |
| 5 | Isopropyl acetate | 71 |
| 6 | Methylene chloride | 77 |
| 7* | Methylene chloride | 82 |

*This experiment is a 250 mmol batch, while the other experiments were carried out with 55 mmol chloropyrimidine.

EXAMPLE 8

4.8 g of sodium hydride were suspended several times and stirred in n-hexane in a sulphonation flask flushed with argon. After removal of the n-hexane it was taken up in 40 ml of DMSO and dissolved with 13.94 g of ethyl acetoacetate and a further 10 ml of DMSO were added dropwise over 1 h. 45 min. 11.49 g of 2-chloropyrimidine dissolved in 10 ml of DMSO are added dropwise to the mixture. Subsequently, 1.16 g of DABCO dissolved in 10 ml of DMSO were added dropwise.

The reaction was controlled by withdrawing samples. After less than 3% of the educt used was present in the reaction mixture the reaction was interrupted and the reaction mixture containing 3-oxo-2-pyrimidin-2-yl-butyr-ethyl ester as the product and the starting, materials was worked up by extraction with toluene and water.

EXAMPLE 9

4.58 g of sodium hydride are suspended and stirred several times in n-hexane in a sulphonation flask flushed with argon. After removal of the n-hexane it is taken up in 40 ml of DMSO and dissolved with 7.08 g of malonic acid dinitrile and a further 10 ml of DMSO are added dropwise over 45 min. 11.5 g of 2-chloropyrimidine dissolved in 10 ml of DMSO are added dropwise to the mixture. Subsequently, 1.16 g of DABCO dissolved in 10 ml of DMSO are added dropwise.

The reaction was controlled by the withdrawal of samples. After less than 3% of the educt used was present in the reaction mixture the reaction was interrupted and the reaction mixture was worked up by extraction with toluene and water. 2-Malononitrile-pyrimidin-2-yl was obtained as the product.

EXAMPLE 10

2-Chloropyrimidine is reacted with 1.05 equivalents of sodium cyanide in the presence of 0.1 equivalent of ABCO in an aqueous solution of DMSO and water at a temperature of 25–30° C. over a period of 4–5 hours.

The working up of the reaction mixture is effected by extraction with TBME. 2-Cyanopyrimidine is obtained.

EXAMPLE 11

2-Cyanopyrimidine can be converted as follows into the endothelin inhibitor bosentan (4-tert.-butyl-N-6-(2-hydroxy-ethoxy)-5-(2-[-methoxy-phenoxy)-2-(pyrimidin-2-yl)-pyrimidin-4-yl]-benzenesulphonamide) (EP-A-526 708):

2-Cyanopyrimidine is converted using NH$_3$, sodium methanolate/methanol solution and ammonium chloride in a known manner into pyrimidin-2-carboxamidine hydrochloride, which is converted in the presence of sodium methanolate with diethyl (o-methoxy-phenoxy-malonate) into rac-5-(2-methoxy-phenoxy)-2-pyrimidin-2-yl-tetrahydro-pyrimidin-4,6-dione.

rac-5-(2-Methoxy-phenoxy)-2-pyrimidin-2-yl-tetrahydro-pyrimidin-4,6-dione is converted with N,N-diisopropyl-N-ethylamine and phosphorus pentachloride into 4,6-dichloro-5-(2-methoxy-phenoxy)-2,2'-bipyrimidine and this is converted with butylbenzenesulphonamide into 4-tert.-butyl-N-6-chloro-5-[2-(2-methoxy-phenoxy)-2-pyrimidin-2-yl)-pyrimidin-4-yl]-benzenesulphonamide). Therefrom using sodium ethylene glycolate there is obtained (4-tert.-butyl-N-6-(2-hydroxy-ethoxy)-5-(2-methoxy-phenoxy)-2-(pyrimidin-2-yl)-pyrimidin-4-yl-benzenesulphonamide) (bosentan).

The subject invention has been described in terms of its preferred embodiments. Upon reading the present specification, various alternative embodiments will become obvious to the skilled artisan. These variations are to be considered within the scope and spirit of the invention which is only to be limited by the claims that follow and their equivalents.

What is claimed is:

1. A compound of the formula:

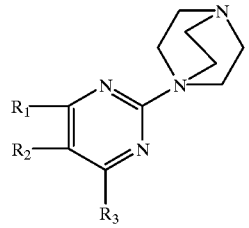

IV wherein $R^1$, $R^2$, $R^3$ each independently is hydrogen, $C_{1-7}$-alkyl, or $C_{1-7}$-alkoxy, and salts thereof.

2. The compound according to claim 1, wherein $R^1$, $R^2$ and $R^3$ are each independently hydrogen, $C_{1-3}$-alkyl, or $C_{1-3}$-alkoxy.

3. A compound according to claim 2 which is 1-pyrimidin-2-yl-4-aza-1-azonium-bicyclo[2,2,2]octane chloride.

4. A compound of the formula:

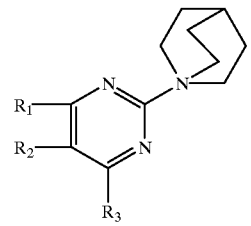

V wherein $R^1$, $R^2$, $R^3$ each independently is hydrogen, $C_{1-7}$-alkyl, or $C_{1-7}$-alkoxy, and salts thereof.

5. The compound according to claim 4, wherein $R^1$, $R^2$ and $R^3$ are each independently hydrogen, $C_{1-3}$-alkyl, or $C_{1-3}$-alkoxy.

6. A compound according to claim 5 which is 1-pyrimidin-2-yl-1-azonium-bicyclo[2,2,2]octane chloride.

* * * * *